(12) United States Patent
Hänninen et al.

(10) Patent No.: US 6,361,956 B1
(45) Date of Patent: *Mar. 26, 2002

(54) BIOSPECIFIC, TWO PHOTON EXCITATION, FLUORESCENCE DETECTION AND DEVICE

(75) Inventors: Pekka Hänninen, Turku (FI); Erkki Soini, Krypingintie 20, 21610 Kirjala (FI); Juhani Soini, Turku (FI)

(73) Assignee: Erkki Soini, Kirjala (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/297,578

(22) PCT Filed: Nov. 18, 1997

(86) PCT No.: PCT/FI97/00704

§ 371 Date: May 5, 1999

§ 102(e) Date: May 5, 1999

(87) PCT Pub. No.: WO98/25143

PCT Pub. Date: Jun. 11, 1998

(30) Foreign Application Priority Data

Dec. 3, 1996 (FI) .................................................. 964826
Apr. 17, 1997 (FI) .................................................. 971626

(51) Int. Cl.$^7$ ........................ G01N 33/53; G01N 33/00; G01V 5/00; G01J 3/30

(52) U.S. Cl. ........................ 435/7.1; 436/172; 436/501; 436/513; 436/518; 436/524; 436/536; 422/68.1; 422/73; 422/82.05; 250/298; 250/396; 250/397; 250/458.1; 250/459.1; 250/461.1; 250/461.2; 356/4.01; 356/4.05; 356/73; 356/213; 356/317; 356/318; 356/336; 356/337; 356/341; 356/342; 356/441; 356/442; 356/945

(58) Field of Search .......................... 549/223; 356/213, 356/317, 318, 441, 442, 4.01, 4.05, 430, 336, 337, 341, 342, 73, 945; 422/68.1, 73, 82.05; 436/501, 513, 518, 524, 536, 172, 800; 250/298, 396, 397, 458.1, 459.1, 461.1, 461.2; 435/7.1

(56) References Cited

U.S. PATENT DOCUMENTS 4,760,548 A * 7/1988 Baker et al. ................. 364/718

(List continued on next page.)

FOREIGN PATENT DOCUMENTS

EP     666473     8/1995

(List continued on next page.)

Primary Examiner—Long V. Le
Assistant Examiner—Kartic Padmanabhan
(74) Attorney, Agent, or Firm—James C. Lydon (57) ABSTRACT

A method for measuring the end point and for monitoring the real time kinetics of a bioaffinity reaction in biological fluids and suspensions, employing microparticles as bioaffinity binding solid phase, biospecific reagent labelled with a fluorescent label and a fluorescence detection system which is based on two-photon fluorescence excitation, contacting the analyte, the labelled reagent and the solid phase simultaneously, focusing a two-photon exciting laser beam into the reaction suspension and measuring the fluorescence signal emitted by the microparticles from one particle at a time when they randomly float through the focal volume of the laser beam. In this method the signal is monitored kinetically to obtain information about the analyte concentration before the reaction approaches the highest point of the response. Since the growth rate of the signal intensity is directly proportional to the analyte concentration, the analyte concentration can be predicted in the initial phase of the reaction. The growth rate monitoring also predicts whether the analyte concentration is higher than the binding capacity of the reagent and whether the reaction will be continued over the highest point of the response curve.

18 Claims, 7 Drawing Sheets

U.S. PATENT DOCUMENTS

| | | | | |
|---|---|---|---|---|
| 5,100,627 A | * | 3/1992 | Bulcan et al. | 422/108 |
| 5,171,688 A | * | 12/1992 | Hewett et al. | 435/289 |
| 5,198,369 A | * | 3/1993 | Itoh et al. | 436/534 |
| 5,469,255 A | * | 11/1995 | Kamada et al. | 356/300 |
| 5,512,745 A | * | 4/1996 | Finer et al. | 250/251 |
| 5,620,857 A | * | 4/1997 | Weetall et al. | 435/7.1 |
| 5,631,141 A | * | 5/1997 | Sonek et al. | 435/29 |
| 5,674,743 A | | 10/1997 | Ulmer | 435/288.7 |

FOREIGN PATENT DOCUMENTS

| | | | |
|---|---|---|---|
| EP | | 723146 | 7/1996 |
| WO | WO 94/16313 | | 7/1994 |
| WO | WO 96/22521 | | 7/1996 |
| WO | WO 96/22531 | | 7/1996 |
| WO | WO 96/27798 | | 9/1996 |
| WO | WO 98/25143 | * | 6/1998 |

* cited by examiner

(1)  $Ab + Ag \underset{k_2}{\overset{k_1 \Rightarrow}{\Leftarrow}} AbAg$     $k_2 = k_1/K_1$ (2)  $Ab^* + Ag \underset{k_4}{\overset{k_3 \Rightarrow}{\Leftarrow}} Ab^*Ag$     $k_4 = k_3/K_3$ (3)  $Ab^* + AgAb \underset{k_6}{\overset{k_5 \Rightarrow}{\Leftarrow}} AbAgAb^*$     $k_6 = k_5/K_5$ (4)  $Ab + AgAb^* \underset{k_8}{\overset{k_7 \Rightarrow}{\Leftarrow}} AbAgAb^*$     $k_8 = k_7/K_7$ (5)  $dx_1/dt = -k_1 x_1 x_2 + k_2 x_4 - k_3 x_1 x_3 + k_4 x_5$ (6)  $dx_2/dt = -k_1 x_1 x_2 + k_2 x_4 - k_7 x_2 x_5 + k_8 x_6$ (7)  $dx_3/dt = -k_3 x_1 x_3 + k_4 x_5 - k_5 x_3 x_4 + k_6 x_6$ (8)  $dx_4/dt = +k_1 x_1 x_2 - k_2 x_4 - k_5 x_3 x_4 + k_6 x_6$ (9)  $dx_5/dt = +k_3 x_1 x_3 - k_4 x_5 - k_7 x_2 x_5 + k_8 x_6$ (10)  $dx_6/dt = +k_5 x_3 x_4 - k_6 x_6 + k_7 x_2 x_5 - k_8 x_6$ (11)  
$[Ag] = x_1$  
$[Ab] = x_2$  
$[Ab^*] = x_3$  
$[AgAb] = x_4$  
$[AgAb^*] = x_5$  
$[AbAgAb^*] = x_6$ (12)  
$[x] = mol\ L^{-1}$  
$[dx/dt] =$  
$[k_{1,3,5,7}] = L\ mol^{-1}\ s^{-1}$  
$[k_{2,4,6,8}] = s^{-1}$  
$[K_{1,3,5,7}] = L\ mol^{-1}$

BIOSPECIFIC, TWO PHOTON EXCITATION, FLUORESCENCE DETECTION AND DEVICE

This is the U.S. National Stage Application of PCT/FI97/00704 filed on Nov. 18, 1997.

BACKGROUND OF THE INVENTION

Immunoassay is an established biospecific assay method, widely used in routine diagnostics and research laboratories. Another group of biospecific assays is DNA and RNA hybridisation assays. Two biospecific probes, a primary probe and a secondary probe (i.e. an antibody, DNA or RNA probe) are usually used in biospecific assays. They are both connected to the specific determinants of the analyte molecules and form a complex of three molecules (sandwich structure). Normally, one of these two reagents is labelled. Nowadays, commonly used labels are radioisotopes, enzymes, luminescent and fluorescent labels. The most common sample material, which is assayed, is blood serum.

The method according to this invention refers to those fluorometric biospecific assays where one biospecific reagent is attached to microparticles serving as a solid matrix. The solid matrix with the attached components is later referred to as the solid phase. The second biospecific reagent is labelled with a fluorescent label and is later referred simply as the label. In regard to their functional principles, assays can be divided in two main groups: 1) assays which have excess reagent bound to a solid phase, which in immunology are called immunometric assays, and 2) assays which have a limited amount of reagent bound to a solid phase. These are referred to as competitive assays.

The first type is applicable for the analyte molecule Ag which can provide at least two specific determinants. In this type of assay, the initial concentration of the biospecific reagent Ab bound to the solid phase exceeds the amount of the analyte Ag. The other reagent in the reaction is the labelled reagent Ab*. Complexes AbAgAb* are bound to the solid phase, and the signal response of the assay is linear. DNA- and RNA-assays are also performed according to the same principle.

The second type is applicable to small analyte molecules Ag. In this assay, the biospecific reagent Ab bound to the solid phase A, is in a limited concentration in relation to the analyte. The other reagent in the reaction is the labelled analyte molecule Ag*, i.e. the labelled analyte molecule is used as the reagent. The components Ag and Ag* bind to the solid phase reagent Ab in proportion to their relative concentrations. This reaction is known as a competitive binding reaction, and the signal response of this type of assay is non-linear.

In addition to these two main groups, the method of this invention is applicable to study the reaction kinetics between different biomolecules Ab and Ab*, i.e. to monitor the formation of reaction products as a function of time. In these studies, we simply monitor how the labelled molecule Ab* binds to the solid phase molecule Ab.

The previously used symbols Ab, Ag and Ab* used here refer to biospecific molecules in general, and are not restricted to immunological antibodies and antigens.

The problem with conventional assays and research methods lies in their complexity. For example, the determination of hormones from blood with a fluorometric immunometric assay method often requires several steps: separation of cells from the serum, dispension and dilution of the serum sample, incubation with the solid phase, separation of the free fraction by washing, incubation with the label, separation of the free label by washing, addition of a measurement solution and measurement of the signal.

Separation of cells from serum is necessary because in conventional fluorometric assays the strong light absorption of haemoglobin affects measurements. In the first type of assays referred to above, the reagents must be added in two separate phases, including separation of the free fraction from the bound fraction between these steps, otherwise the assay response, (i.e. the concentration of the product AbAgAb*) is decreased if the analyte concentration exceeds the binding capacity of the solid phase. This harmful phenomenon appears only when all assay components are added simultaneously, and is called the "hook effect" in the literature. The free label must also be separated; otherwise the signal from the bound label can not be measured because of the high background signal contributed by the free label.

There is a constant need for simpler and more cost-effective analyses within routine diagnostics. The new biospecific assay method of the present invention using fluorescent labels involves only one step, and does not require separation of the label, and is particularly suitable for assays in whole blood or in other biological suspensions. In addition, this invention makes it possible to perform real-time measurements of bioaffinity reaction kinetics.

Two-photon Excitation

Two-photon excitation is created when, by focusing an intensive light source, the density of photons per unit volume and per unit time becomes high enough for two photons to be absorbed into the same chromophore. In this case, the absorbed energy is the sum of the energies of the two photons. According to the concept of probability, the absorption of a single photon in a dye, is an independent event, and the absorption of several photons is a series of single, independent events. The probability of absorption of a single photon can be described as a linear function as long as the energy states that are to be excited are not saturated. The absorption of two photons is a non-linear process. In two-photon excitation, dye molecules are excited only when both photons are absorbed simultaneously. The probability of absorption of two photons is equal to the product of probability distributions of absorption of the single photons. The emission of two photons is a thus a quadratic process.

The properties of the optical system used for fluorescence excitation can be described with the response of the system to a point-like light source. A point-like light source forms, due to diffraction, an intensity distribution in the focal plane characteristic to the optical system (point spread function). When normalised, this point spread function is the probability distribution of how the photons from the light source reach the focal area. In two-photon excitation, the probability distribution of excitation equals the normalised product of intensity distributions of the two photons. The probability distribution thus derived, is 3-dimensional, especially in the vertical direction, and is clearly more restricted than for a single photon. Thus in two-photon excitation, only the fluorescence that is formed in the clearly restricted 3-dimensional vicinity of the focal point is excited.

When a dye is two-photon excited, the scattering of light in the vicinity of the focal point and from the optical components, is reduced remarkably compared to normal excitation. Furthermore, two-photon excitation decreases the background fluorescence outside the focal point, in the surroundings of the sample and in the optics. Since the exciting light beam must be focused onto as a small point as possible, two-photon excitation is most suitable for the observation of small sample volumes and structures, which is also the case in the method according to this invention.

The advantage of two-photon excitation is also based on the fact that visible or near-infrared (NIR) light can, for example, be used for excitation in the ultraviolet or blue region. Similarly, excitation in the visible region can be achieved by NIR light. Because the wavelength of the light source is considerably longer than the emission wavelength of the dye, the scattering at a wavelength of the light source and the possible autofluorescence can be effectively attenuated by using low-pass filters (attenuation of at least 10 orders of magnitude) to prevent them from reaching the detector.

Since in two-photon excitation the density of photons per unit volume and per unit time must be very high in order to make two photons to be absorbed into the same chromophore, it is useful to use lasers which generate short pulses with high repetition rate. A practical laser for two-photon excitation is for example a passively Q-switched Nd:YAG laser with a pulse length of 1 ns.

OBJECT AND SUMMARY OF THE INVENTION

The object of this invention is related to an improved biospecific assay method and device employing microparticles as solid phase. Another object of this invention is to improve the multiparametric method and device as described by the inventors in international patent publication WO 96/22531. In the method according to the present invention, the biospecific reagent is labelled with a fluorescent label. The fluorescence excitation is based on two-photon excitation. Since two-photon excitation is restricted to a diffraction limited focal volume, only one microparticle at a time fits in the two-photon excited focal volume, and the free labels outside the focal volume do not contribute any significant background signal.

The method and device referred to above and described in patent publication WO 96/22531, allows a separation free assay for very small sample volumes but the methodological and instrumental set-up of the assay system in the presented form requires a complicated microfluidics system. The objective of this invention is to further improve said method and device. In order to make the method and device even more simple and cost-effective, the improvement of this invention is relative to following design requirements:

1) Because of the growing interest to avoid centifugal separation of the blood serum, the assay performed in whole blood or other cell suspensions without separation of the cells becomes more potential.
2) Simplification of the liquid handling system reduces strongly the system cost.
3) Diagnostic concentrations of certain analytes cover very large dynamic range. In addition a multiparametric assay system should allow simultaneous measurement of different analytes—one analyte having its clinical reference concentrations at the low end, and another analyte having its clinical reference concentrations at the high end. Consequently the total dynamic range needed is of several orders of magnitude.
4) The assay should be fast. This means that the microparticles should be measured at high rate and the signal obtained from each particle should be high enough.

The crucial point of the method of this invention is that the assay can simply be performed by focusing the laser beam directly to the reaction suspension and the formation of the complexes on the surface of the microparticles can be monitored without the need of complicated liquid handling and flow systems. This invention leads to a remarkable methodological simplification but it also allows many other useful features which satisfy the assay requirements defined above and which will be discussed later in this text.

The essential features of the invention are presented in claims.

The method of the present invention is related to measuring the end point and to monitoring the real time kinetics of a bioaffinity reaction in biological fluids or suspensions. The method employs microparticles as bioaffinity binding solid phase to which a primary biospecific reagent is bound, a biospecific secondary reagent labelled with a fluorescent molecule or with a fluorescent nanoparticle and a fluorescence detection system which is based on two-photon fluorescence excitation. The microparticles are contacted with the analyte and the labelled secondary reagent simultaneously in the reaction volume, initiating formation of the reaction products of said components. For obtaining a signal relative to the analyte concentration, a two-photon exciting laser beam is focused into the reaction suspension and the fluorescence emission is measured from the single microparticles when they randomly float through the focal volume of the laser beam.

The device needed for carrying out the method of the present invention performs measurement of the end point or monitors the real time kinetics of the bioaffinity reaction. The device incorporates a means for generating a two-photon exciting laser beam which can be focused into the reaction suspension for measuring the fluorescence emission from the single microparticles when they randomly float through the focal volume of the laser beam.

DETAILED DESCRIPTION OF THE INVENTION

Preferred Embodiments

The efficiency of the measurement can be improved by active trapping techniques which means that that the microparticles are trapped for the period of fluorescence detection with an optical trap which preferably is performed with same laser beam as used for the two-photon fluorescence excitation. The duty cycle of trapping can be improved by a mechanical or optical scanner which moves the sample containing the microparticles in relation to the focal point and the scanner movement can be controlled by a signal obtained from a confocal detector measuring light scattering or reflection from the microparticles and the speed of scanning is reduced for the period of measuring the fluorescence emission.

The method of the present invention is related to improve the dynamic range of the assay by performing following steps:

during the initial period of the reaction before the reaction approaches equilibrium a parameter g indicative to the signal growth rate is registered at one or at several time points or within a period of time and the signal response R of the labeled reaction product is measured in the end point of the reaction and the concentration p of the analyte P is determined on the basis of the standard curve $p=R'(R)$ or $p=G'(g)$ if the concentration of the analyte is lower or higher than the concentration of the primary reagent, respectively. The growth rate of signal intensity is determined by fitting a polynomial function to the curve of the signal intensity measured as a function of time and the concentration of the analyte p will be determined from the coefficients of said polynomial function. If the fitted function is of first order, the concentration of the analyte is determined from the slope of said function.

According to a preferred embodiment, the device comprises an objective lens and a laser that can be focused into the reaction volume through said objective lens for performing an optical trap for the microparticles and the laser power and the numerical aperture of the objective lens have been optimised for performing the optical trap within the two-photon excitation focal volume. The device can incorporate a mechanical or optical scanner, controlled by a trigger signal obtained from the light scattering detector, for moving the sample containing the microparticles in relation to the focal point and a control system for reducing the scanning speed for the period of fluorescence detection. The light scattering detector is confocal with the laser beam. The device can incorporate a flat thin substrate, e.g. plastic foil, onto which the reaction components are dispensed and that the material of the substrate can be chosen from a hydrophobic material which allows the surface tension of the liquid to keep the reaction volume on the surface in form of a droplet.

The method can be carried out as e.g. as follows: The sample including the analyte to be determined and the biospecific labelled reagent are simultaneously contacted with the microparticles which are coated with the biospecific reagent. Due to bioaffinity, complexes composed of the analyte and labelled biospecific reagent are bound to the solid phase on the surface of the microparticles. The components of the reaction suspension are dispensed on the surface of a thin transparent substrate allowing a light beam from a pulsed near infrared (NIR) laser to be focused through the substrate into the reaction suspension. The volume of the reaction suspension is small enough, for example 1 $\mu$L, for keeping the reaction volume as a droplet on the flat surface or in a shallow well.

Since the focal volume of the laser beam is restricted by diffraction, the light beam is focused only on a single microparticle at a time. Due to movements of the suspension, the microparticles randomly move in and out of the focal volume. The label on the surface of each microparticle which float into the focal volume, is excited by two-photon absorptions and its fluorescence emission is measured with a photon detector. The signal relative to the photon count rate obtained from the detector is dependent on the reaction rate and on the concentration of the analyte in question. By following the signal growth, it is possible to obtain information about kinetic reaction parameters and about analyte concentration before the reaction has reached equilibrium.

Direct Measurement of Complex Formation in the Reaction Volume

The use of monodispersive microparticles as the solid phase in this biospecific assay ensures a rapid bioaffinity reaction. Since in the reaction, which occurs on the surface of the microparticles, the average distance between the reaction components is very small, the reaction equilibrium is reached quickly. Monodispersive spherical microparticles with diameter of 0.01–100 $\mu$m can be produced from appropriate polymer, glass and other optically transparent material so that they are well suited for water suspensions. Suitable surface properties can be provided for binding of macromolecules by physical adsorption as well as by covalent coupling.

The microparticles that function as solid phase of the biospecific reaction, are in a continuous random movement in the suspension including the sample and reagent. This movement, called diffusion, is caused by thermal vibrational forces. As course of the diffusion, the particles randomly float through the two-photon excitation focal volume and a signal that is proportional to the amount of the fluorescent label on the surface of the microparticle, is registered. The duration of the fluorescence signal depends on the transit time, i.e. the time a microparticle remains in the focal volume. The expected duration of the transit time for 3 $\mu$m particles as calculated on the basis of the diffusion theory, is in the order of one millisecond.

We have observed, however, that when the microparticles are let randomly float through the focal volume by free diffusion, the transit time can be in the order of 300 ms for 3 $\mu$m particles. This led to a discovery that the strong laser beam that was needed for two-photon excitation, functions as an optical trap either in two or three dimensions depending on the laser power and on the numerical aperture of the objective lens. The three-dimensional trap allows a long trapping time until the particle is released from the trap. This can be accomplished for example by switching off the laser for a short period of time.

The optical trapping effect is based on the radiation pressure and repulsion forces caused by the laser radiation. The direction and strength of the trapping forces depend on the size, shape and refractive index of the particle. In addition the wavelength of the radiation as well as the light absorbance and reflectance of the particle play an important role. A laser beam with very tight focus will form trapping forces both in axial and lateral directions. A laser beam with a smaller focusing angle (low numerical aperture of the focusing lens) will form trapping forces in lateral direction and propulsion forces in axial direction. In this later case, when a microparticle is floating into the vicinity of the focal volume, it will fall into the two dimensional potential well inside the focal volume and it remains there until it is pushed out from the focal volume by the propulsion forces. The theory and applications of the optical trap have been described in the literature (Ashkin A., Phys.Rev.Lett. 24(4): 156, 1970 j a Ashkin, A., Dziedzic, J. M., Bjorkholm, J. E., and Chu, S. Opt.Lett. 11(5):288, 1986).

Figure 1:
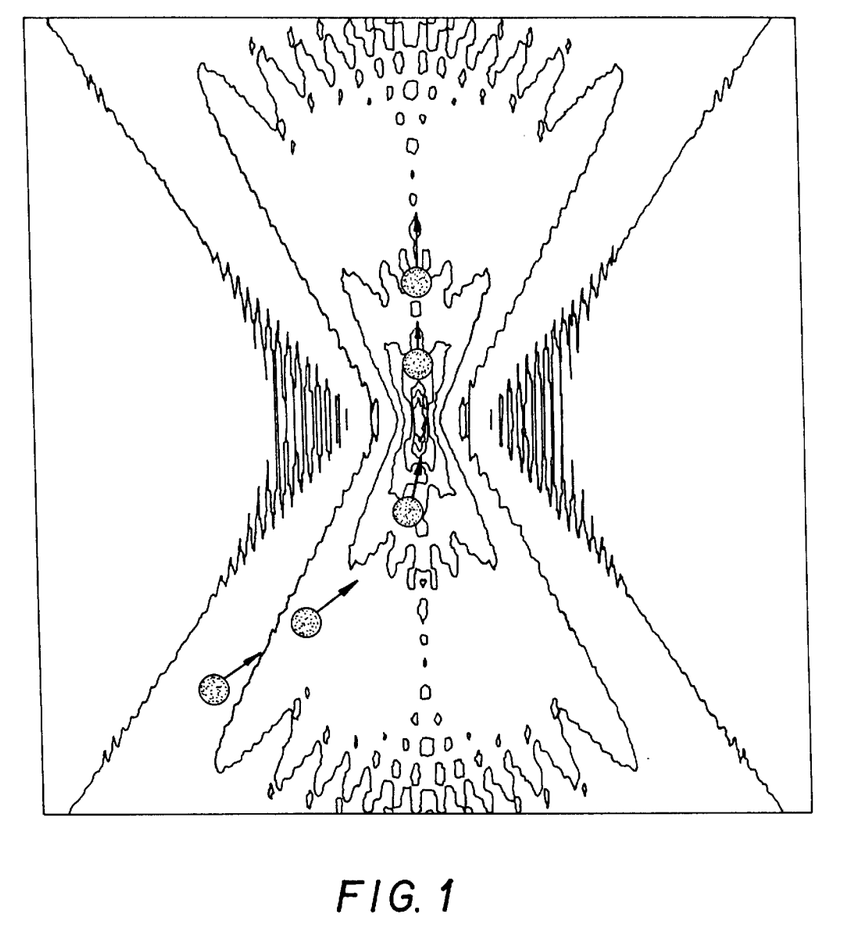
FIG. 1 shows the migration path of a particle through a laser beam's ellipsoid-shaped two-photon excitation volume, with the laser beam being focused through an objective lens having a numerical aperture of 0.65, the laser intensity profile being shown in the two dimensional case, and the vertical axis being the direction of the laser beam.

FIG. 1 presents a contour model for the double funnel shaped laser intensity profile (point spread function) around the focal point in the two dimensional case. The vertical axis is the direction of the laser beam. The contours indicate the relative intensity distribution. The model has been calculated on the basis of the theory as presented by Richards & Wolf 1959 that can be found for example in: Stamnes, J. J.

(1986), Waves in focal regions: Propagation, Diffraction and Focusing of Light, Sound and Water Waves, pp. 461-. Bristol, England: Adam Hilger Imprint by IOP Publishing Limited. The dimension of one scale unit is 4 µm. The numerical aperture of the objective lens for this model is 0.65. The radiation pressure exposed to a particle is sucking the particle into the ellipsoid shaped two-photon excitation volume and then pushing it out in direction of the vertical axis. FIG. 1 shows how a 3 µm particle will migrate through the funnel and how it moves through the centre of the focal point and how it remains a relative long time under two-photon excitation. The use of the two dimensional trap leads in any case to a much longer average transit time than if the particle was affected only by transversal diffusion. Consequently the total number of photon counts during the transit time is larger than without trapping effect.

In our experiment, same laser functioned for two-photon excitation of the fluorescent dye and as a means for a two dimensional optical trapping of the microparticles. In this experiment we used a passively Q-switched Nd:YAG laser producing 30 mW at 1064 nm wavelength and objective lenses of numerical aperture of 0.65 to 0.8.

The trapping effect in the context of this invention was found very important since it increases the total counts of detected photons. Since the microparticles remain a longer time in the focal volume and a larger portion of randomly moving particles will float through the centre of the focal point, the variance of the counts obtained from different particles is smaller.

Assaying Whole Blood and Other Cell Suspensions

It is known that the background signal caused by scattering and auto-fluorescence can be eliminated by using two-photon excitation (WO 96/22531). Surprisingly, we have discovered that the excitation light, for example, at 1064 nm wavelength, does not provoke fluorescence of hemoglobin (protoporphyrin IX), and therefore the background fluorescence caused by red cells is not significant even when the microparticle suspension contains a remarkable amount of red cells. It is clear that the light absorption in the NIR-range by red cells and in particular that of haemoglobin is very small, but more interestingly, the two-photon excitation energy transfer mechanism of porphyrines seems to be totally different than that of single photon excitation, and consequently the autofluorescence of red cells in the suspension contributes surprisingly low or even negligible background signal.

The observation relative to the difference between single photon and two-photon fluorescence excitation of porphyrines led to a possibility to eliminate the need of separation of the cells and to perform the assay directly in cell suspension without any significant interference caused by the autofluorescence.

Simplification of the Liquid Handling System

Another possibility offered by concept of this invention is the simplification of the liquid handling system. This can be accomplished simply by focusing the two-photon exciting laser beam into the reaction volume through a transparent window of the reaction cuvette or substrate. Thus, a fluorescence signal is obtained when a microparticle randomly floats in and out of the focal volume either due to diffusion or liquid movement.

The reaction substrate is made for carrying a large number of samples of very small volumes. The detection system based on two-photon excitation allows very small reaction volumes without any loss of performance and consequently the smallest practical reaction volume is limited by the dispensing techniques and on the evaporation of the sample rather than by detection. It is obvious that a reaction volume in the order of 1 µL would be practical from various points of view. Such a small volume can be dispensed in a shallow well in a fat substrate and this substrate can incorporate a large number of such wells. Alternatively the volume can be dispensed on a flat surface, a disc, plate or foil. If the material of the substrate has been chosen from a hydrophobic material, the surface tension of the liquid keeps the reaction volume on the surface in form of a droplet. The laser beam for two-photon fluorescence excitation will be focused to the reaction volume with a large numerical aperture objective lens and such a lens has a working distance shorter than e.g. 0.3 mm. Therefore the substrate must provide a thin window, preferably thinner than 0.2 mm in order to allow focusing the beam in the suspension. A tape made of suitable plastic foil (e.g. perfluoraethylenpropylen, FEP-foil made by DuPont), is particularly practical because it can be made thin, e.g. 0.05 mm and it is inexpensive and a large amount of such tape can be loaded in the system. The surface forces keep the droplet in a firm position on the surface irrespective of the substrate's position in relation to gravitation. The objective lens can be focused to the droplet through the thin substrate or directly into the droplet.

Dispensing of microvolumes can be performed for example using droplet generators which are based on the use of piezoelectric actuators. A typical droplet generator currently commercially available can make 0.1–1 nL droplets with 1–2 kHz frequency.

Kinetic Monitoring of the Reaction Rate

When focusing a laser beam into the suspension, the fluorescence signal is obtained when a particle is exposed by two-photon excitation. Since the fluorescence signal amplitude is directly proportional to the amount of bound label on the microparticle, this concept functions as real as the monitoring of the reaction kinetics until the equilibrium. The amplitude of the signal obtained from a microparticle also depends on how randomly the floating microparticles intersect the focal volume. Notwithstanding, if a statistically sufficient number of microparticles can be measured in a short time period, it is possible to follow the kinetics of the bioaffinity reaction precisely enough by monitoring the fluorescence intensity.

Increasing the Particle Rate

Many applications of the biospecific assays involve a large number of samples. High sample throughput as well as the kinetic reaction rate monitoring require high yield of signal and a good statistical precision in a short time. When applied to the method of this invention, these requirements lead to the demand of a high particle rate and a short counting time.

In the assay system according to this invention the microparticles may randomly float, for example due to diffusion, into the focal volume of the laser beam. The rate of microparticles floating into the focal volume depends on microparticle concentration. To speed up the measurement, the suspension can be made to move, or the cuvette or any container including the suspension may be stirred or rotated at a desired speed. The faster is the movement, the higher is the rate of particles which randomly float through the focal volume.

The particle rate, the number of particles floating through the focal volume per second, is proportional to the particle concentration. The particle size and concentration in an assay has an optimum which depends on the assay performance parameters and it is favourable to use small particles and relative low concentrations. When using for example 2 µm particles, the optimum particle concentration for the highest performance is less than $10^7$ particles/mL and this is at least one order of magnitude lower than needed for a reasonable particle rate with free diffusion. The fluorescence emission takes place only during the period when the particles moving across the focal volume and are under two-photon excitation. Small particles move faster than large particles and they remain in the focal volume much shorter time. This leads to a definition of excitation duty cycle which is the ratio between the total excitation time and the total elapsed time. In the example given above, the duty cycle is in the order of $10^{-2}$, which is very low. Such a low duty cycle means that the counting is active only for a very small fraction of the elapsed time and consequently the number of photon counts remains low and the total counting time, necessary for required statistical precision, is long.

The particle rate can be increased by moving the suspension or the reaction chamber in respect to the focal point. The particle rate is increased by increasing the speed of the movement. Scanning by up to 100 $\mu$m/s keeps the 3 $\mu$m particle in the two dimensional trap but when increasing the scanning speed, the particle is released from the focal trap. With increased scanning speed, the trapping forces of the optical trap are too small for keeping the particle in the trap because. the optical trapping forces cannot resist the viscosity friction forces. Therefore with increased speed the transit time becomes shorter in the same proportion and the duty cycle remains at the same low level.

We have found, however, that the duty cycle can be improved with the active trapping technique. This is accomplished by using an electronically controlled mechanical or optical scanning system for moving the microparticle suspension in relation to the focal point or vice versa. The movement should be fast enough for bringing a new particle into the focal volume much quicker than the diffusion. A feedback from the detector to the scanning system reduces the scanning speed immediately when the signal caused by the microparticle is detected. The scanning speed is reduced for a short period of time only. If using two dimensional trapping, the scanning speed is reduced for the period of the time equal to the microparticle trapping time in the focal funnel. After this short period the scanning speed is recovered again for finding a new particle.

We have found that by using a mechanical stage scanner for the reaction cuvette and by performing a circular scanning movement with a radius of 0.5 mm, the duty cycle can be improved significantly. Optimising the laser power and numerical aperture of the objective lens, the transit time can be made shorter and the particle rate higher, respectively.

The mechanical trapping scanner can be operated with an electromechanic, galvanometric or piezoelectric actuator. The signal needed for control of the trapping scanner can best be obtained from a scattering detector at the laser wavelength. When using microparticles made of latex or other optically transparent material with high refractive index, the scattering signal is strong. The scattering signal is needed early enough when the microparticle approaches to two-photon excitation focal volume in order to reduce the scanning speed and to allow trapping effect to work. By using a confocal scattering detection system with an appropriate pinhole in front of the scattering detector, it is possible to optimise the size of the spatial scattering response function.

Fluorescence Signal Intensity

Two-photon fluorescence excitation often contributes very low signal level if compared with that of single-photon excitation. A high sensitivity, however, even up to single molecule level, can be obtained because the background signal is also very low. Regardless of sensitivity, a low signal yield may lead to long counting time. For a high throughput and particularly for kinetic monitoring it is important to maximise the signal intensity in terms of detected photons per second. We have found commercially available fluorescent latex nanoparticles very useful for labelling of biospecific reagents. An antibody or a few antibodies can be covalently or passively tagged to such nanoparticle. A nanoparticle with diameter from 10 to 100 n*m can incorporate a large number of fluorescent dye molecules. A 20 nm nanoparticle may incorporate for example 1000 fluorescent molecules and the signal intensity is 1000 times larger than that of a single molecule. In addition the dye molecules inside the microparticle are subject to lower solvent quenching, self quenching and narrower emission bands than the free molecules in solution, and they contribute a higher fluorescence yield and better spectral resolution at same level of excitation.

Large Dynamic Range

The assay signal response R refers to the value of signal intensity I obtained from the label as a function of analyte concentration p. Signal intensity I refers to the intensity of signal obtained from the label at the specific time t. The peak value of signal response refers to the point where the signal response of the assay, i.e. the standard curve, reaches its highest value (point H in FIG. 6).

The problem with conventional assay methods lies in their complexity, and that the dynamics is restricted to values below the concentration of reagents. Normally the reagents must be added into the reaction cuvette in two separate steps and the cuvette must be washed between these steps. The purpose of using two steps and washing is to restrict the assay response to correspond with the binding capacity of the solid phase. This is necessary because in single-step assays, the signal response R decreases when the analyte concentration p exceeds the binding capacity of the primary reagent. As soon as the concentration of analyte Ag exceeds the binding capacity of reagents, in addition to complexes AbAgAb*, the reaction products include complexes AgAb* which are formed in relative proportions to the concentrations of the solid phase Ab and the analyte Ag. The greater the amount of excess Ab in relation to the binding capacity of the. primary reagent Ab, the weaker the assay signal response R. This harmful phenomenon appears only when all assay components are dispensed simultaneously, and is called the "hook effect" in the literature. Because of the hook-effect, the assay response is ambiguous, and therefore, the dynamic range of the system is usually restricted to correspond to the capacity of primary reagent Ab. Moreover, in order to prevent possible false results with the conventional procedures, the potential excess material in the reaction solution is, after the analyte Ag has reacted with the primary reagent Ab, separated from the reaction solution using a suitable method. When one of the reagents is connected to the solid phase, for example, on the surface of the cuvette, the most common separation method is washing the cuvette.

The risk of false results due to the hook-effect has restricted extensive use of single-step assays, although there is a constant need for simpler and more cost-effective analyses within routine diagnostics. The present feature of this invention allows a single-step assay with a dynamic range larger than with conventional multi-step assays and eliminates the risk of false results caused by the hook-effect.

Figure 6:
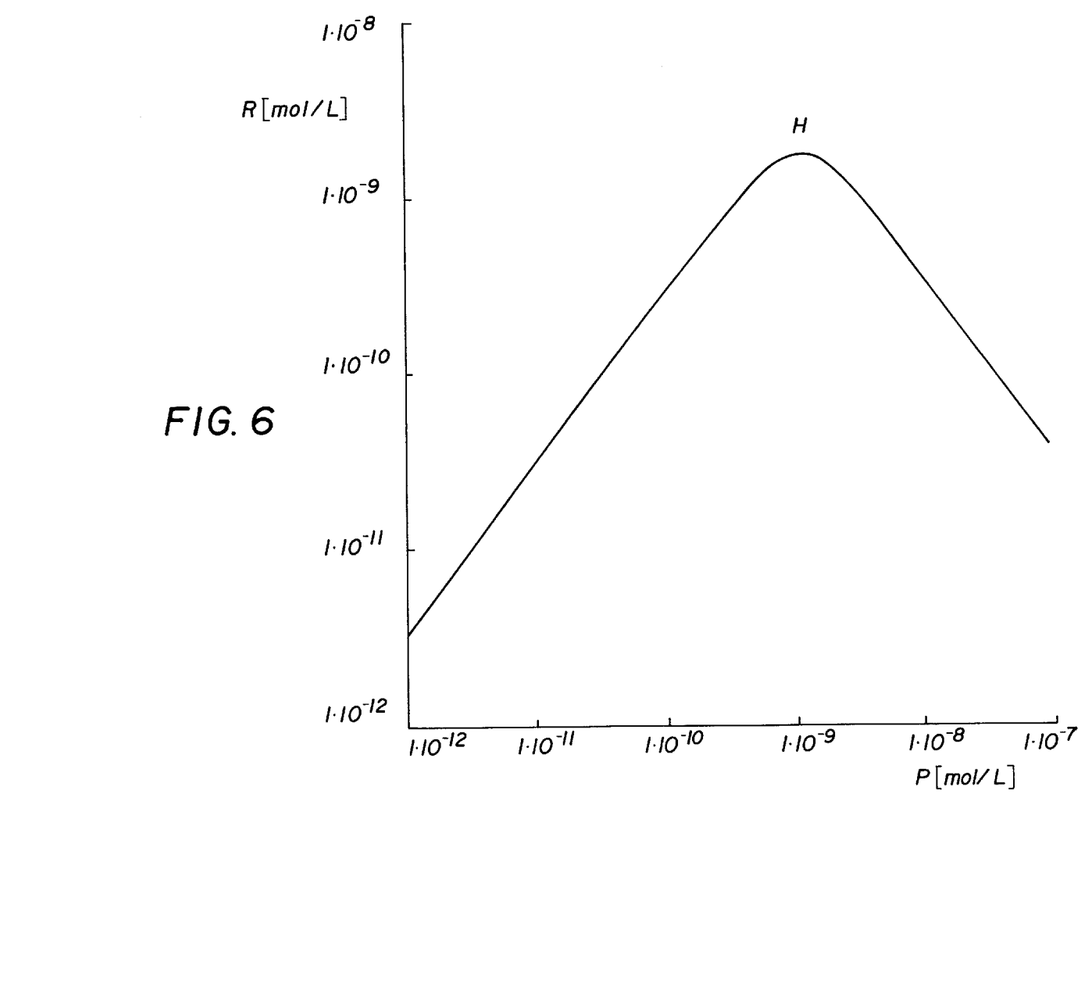
FIG. 6 is a standard curve which represents the concentration R of product AbAgAb* formed in the reaction as a function of concentration p of analyte Ag.
Figure 7:
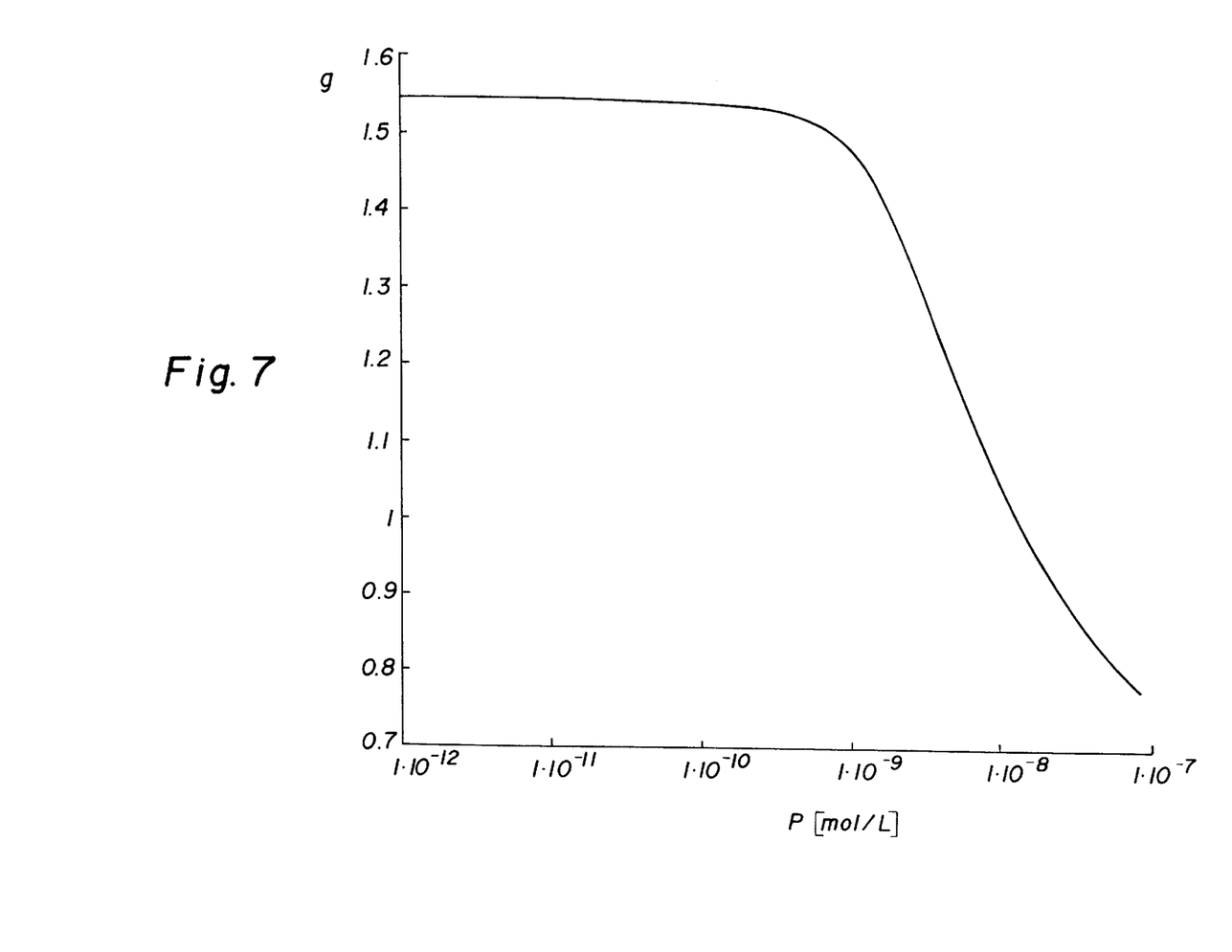
FIG. 7 is a standard curve which represents the kinetic response g of product AbAgAb* formed in the reaction as a function of concentration p of analyte Ag.

Characteristic of the present feature of this invention is that the measurement system presented here, can distinguish optically between the signal emitted from complexes AbAgAb* and the signal emitted from the free labelled reagent. In addition, characteristic of the present feature of this invention, is that the sample, and the primary and secondary reagents are added simultaneously, and the signal intensity of the reaction product is monitored as a function of time from the beginning of the reaction. This is later called kinetic measurement. Kinetic measurement gives us information about the analyte concentration long before the reaction has reached equilibrium. The growth rate $dI/dt$ of the signal intensity is proportional to the initial analyte concentration p, and this information can already be used in the early stages of the reaction to estimate the approximate analyte concentration and more specifically, whether the analyte concentration is higher than the binding capacity of the primary reagent Ab. Thus, the kinetic measurement defines whether the reaction equilibrium is reached on the right or left side of the peak value H in the standard curve (FIG. 6). On th e basis of the reaction kinetics, analyte concentrations exceeding the binding capacity of the solid phase are observed, and thus, it is possible to measure higher analyte concentrations compared to conventional assay methods without risk of false results. The dynamic range of the system can thus be expanded significantly. For example, the normal 3 orders of magnitude dynamic range can be increased with the method of this invention to 5–6 orders.

The actual feature of the invention can be characterised by following steps:

By using known standard samples, two standard curves are measured for calibration purposes. The first standard curve $g=G(p)$ denotes the growth rate $dI/dt$ of the signal intensity I at specific time period $t_1+\Delta t$ as a function of analyte concentrations. The second standard curve $R(t_2, p)$ denotes the value of the signal response after a specific reaction time $t_2$, as a function of the analyte concentration p.

When measuring unknown samples, the signal intensity I is registered as a function of time, and parameter g, which characterises the growth rate of the signal intensity I, is measured. After a specified reaction time, the R is also measured.

When the reaction has advanced close to the equilibrium, the inverse function $p=G'(g)$ of the standard curve $g=G(p)$ is used to determine whether the concentration p of the unknown sample is less than, approximately equal to, or more than concentration q of the solid phase.

If $p<q$, the sample concentration p is read from the standard curve $p=R'(R)$;

if $p=q$, the sample concentration p is read from the standard curve $p=G'(g)$;

and if $p>q$, the sample concentration p is read from either curve.

EXAMPLE

The method described above can be illustrated in more detail using an application example. Reaction charts, reaction equations, standard curves and signal intensity curves presented in FIGS. 2–7 were produced using mathematical modelling.

Figure 2:
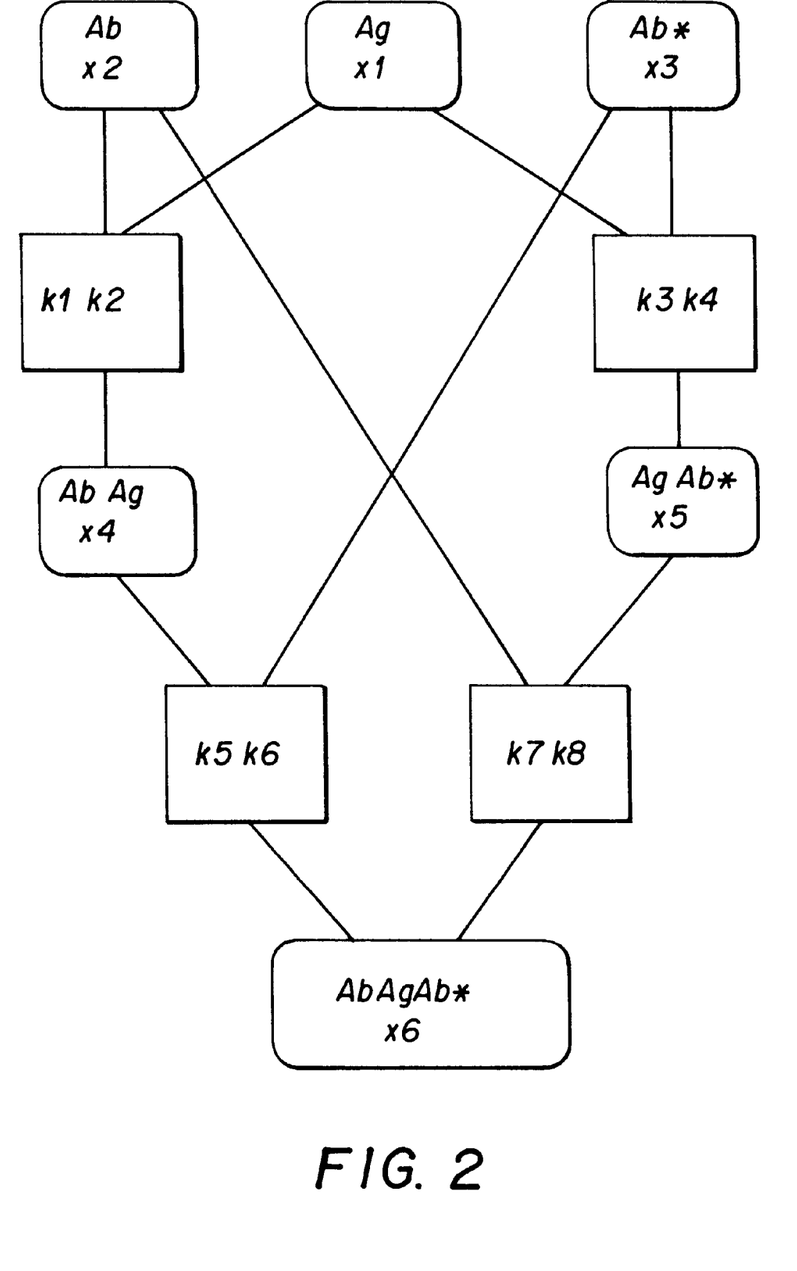
FIG. 2 illustrates the reaction scheme of an assay which simultaneously adds a biospecific reagent Ab bound to a solid phase, analyte Ag and a labelled reagent Ab* to a reaction solution.

As a practical example of this invention, we present an assay which uses a biospecific reagent bound to the solid phase. FIG. 2 shows the reaction scheme of the assay. The initial components of the reaction include a biospecific reagent Ab bound to the solid phase, analyte Ag and a labelled reagent Ab*. Components Ab, Ag and Ab* are added simultaneously in the reaction solution. The reaction equations (formulas 1–4) presented in FIG. 3 cover all the possible reactions and products. Letters k refer to the reaction association and dissociation rates. Reaction rates naturally differ a lot. Reactions occurring in the liquid phase are rapid, whereas reactions associated with the solid phase are slower. In this example, the selected reaction constant values are typical for these types of assays. The selected equilibrium value (affinity) of biospecific reagents Ab and Ab* is $K=1.10^{10}$ L/mol.

Figure 3:
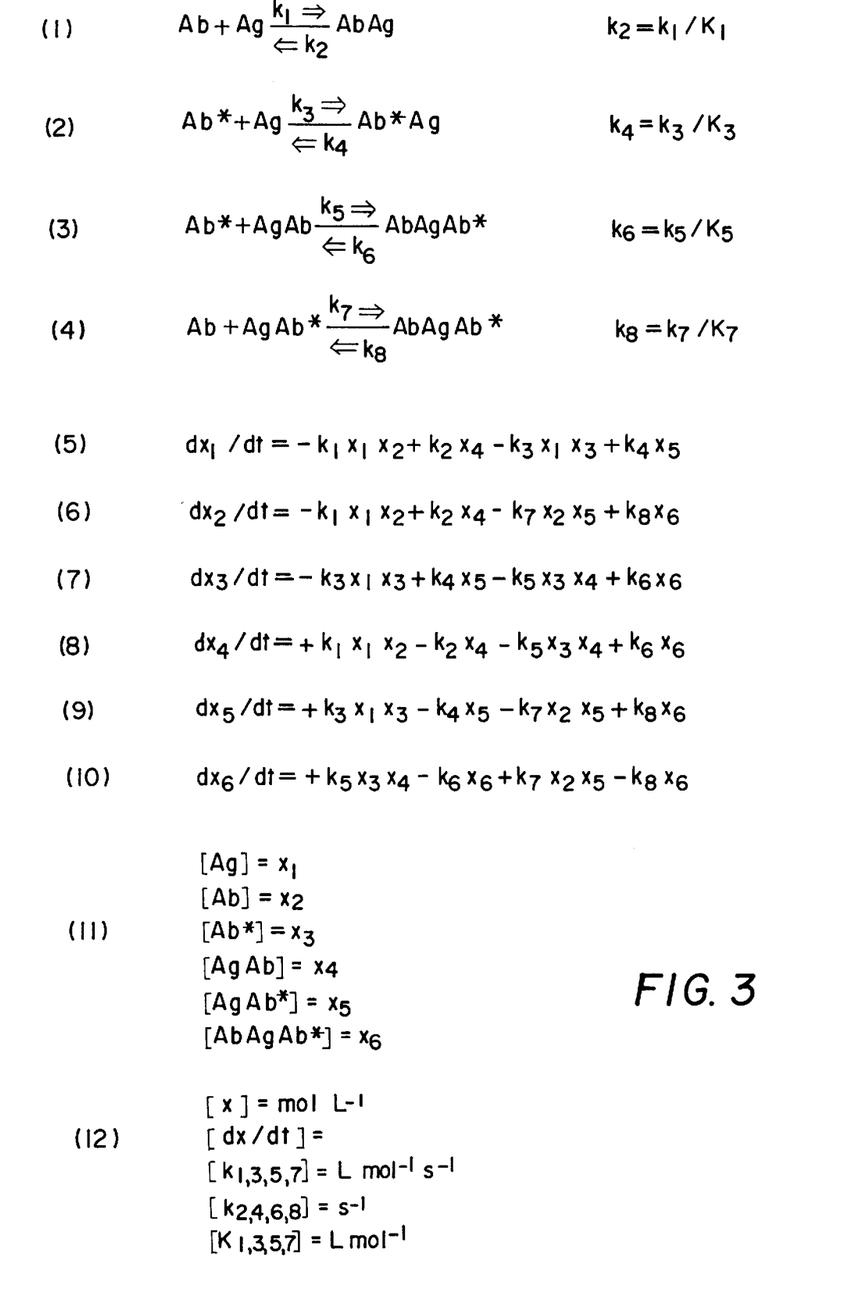
FIG. 3 shows all possible reactions and reaction products of the reaction scheme of FIG. 2.

The selected association rates of different reactions are as follows:

$k_1=1.10^7$ L mol$^{-1}$ s$_{-1}$
$k_3=1.10^9$ L mol$^{-1}$ s$^{-1}$
$k_5=1.10^7$ L mol$^{-1}$ s$^{-1}$
$k_7=1.10^7$ L mol$^{-1}$ s$^{-1}$ Since $k_{diss}=k_{ass}/K$, the selected dissociation constants are:

$k_2=1.10^{-3}$ mol$^{-1}$ s$^{-1}$
$k_4=1.10^{-1}$ mol$^{-1}$ s$^{-1}$
$k_6=1.10^{-3}$ mol$^{-1}$ s$^{-1}$
$k_8=1.10^{-3}$ mol$^{-1}$ s$^{-1}$ In addition, it is assumed that the concentration of reagent Ab bound in the solid phase A is $q=1.10^{-9}$ mol/L and the concentration of the labelled reagent Ab* is $q^*=1.10^{-9}$ mol/L.

For the sake of simplicity, these reaction equations correspond to the reactions in the solution and the association rate constants are assumed to include all diffusion factors. The effect of concentration gradients, due to diffusion, in the end result of this model is minimal, since the solid phase is in the form of microparticles which, in turn, are spread evenly in the suspension, and therefore, the average diffusion distances are very small. It is simply assumed that association and dissociation rates of the reaction with the solid phase are one or two orders slower than the corresponding rates in the solution. This assumption covers the inertia caused by diffusion in the reaction occurring with the solid phase.

FIG. 3 presents differential equations (Equations 5–10) derived from the reaction equations. Their solution illustrates reaction kinetics. The values of variables $x_i$ are given in the system of equations as marked as Equation 11 and the units of terms as marked as Equation 12. Only a numerical solution of these differential equations is possible, and we have used Mathcad 6.0+ mathematics software to solve them (Matsoft Inc., Cambridge, Mass., USA). This mathematical modelling makes it possible to simulate reaction kinetics and consumption and formation of different reaction components under different initial conditions including reaction rate constants and concentrations of the reagents and other possible initial values which might affect the reaction.

Figure 4:
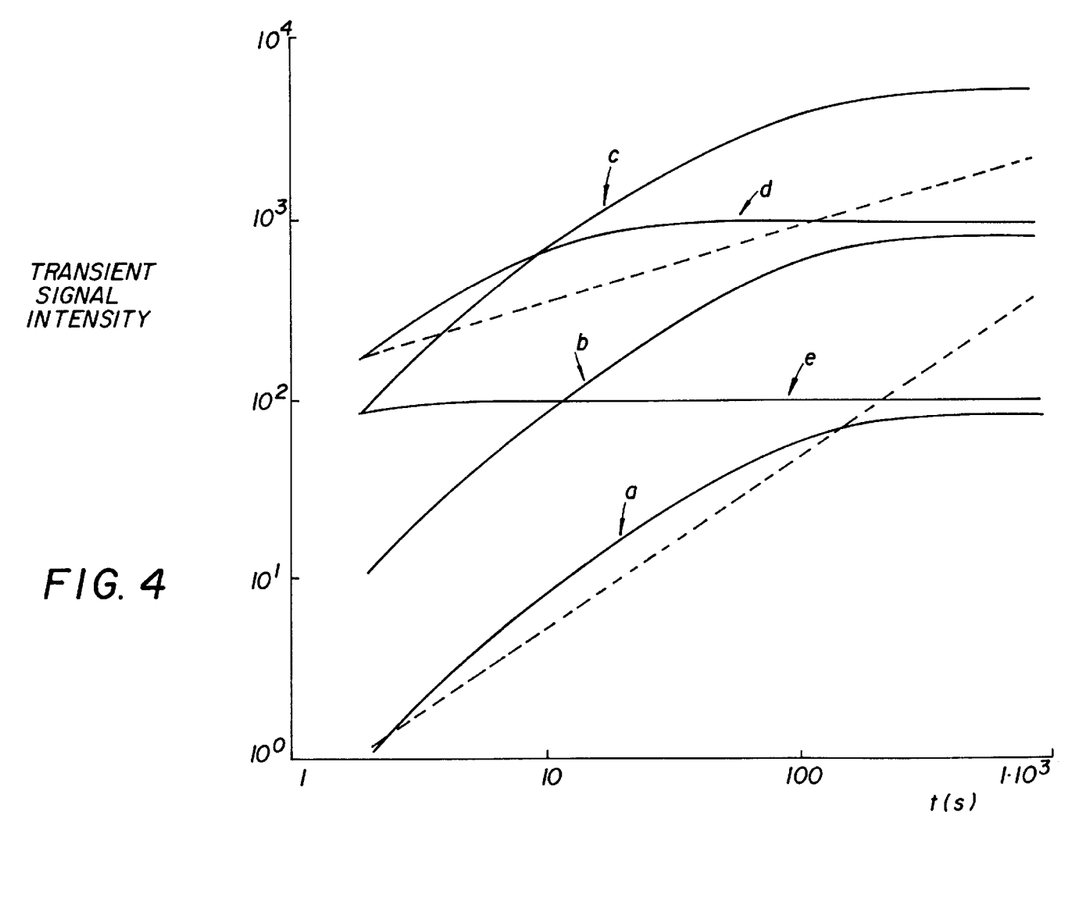
FIG. 4 shows plots of transient signal intensity as a function of time at five different analyte concentrations.
Figure 5:
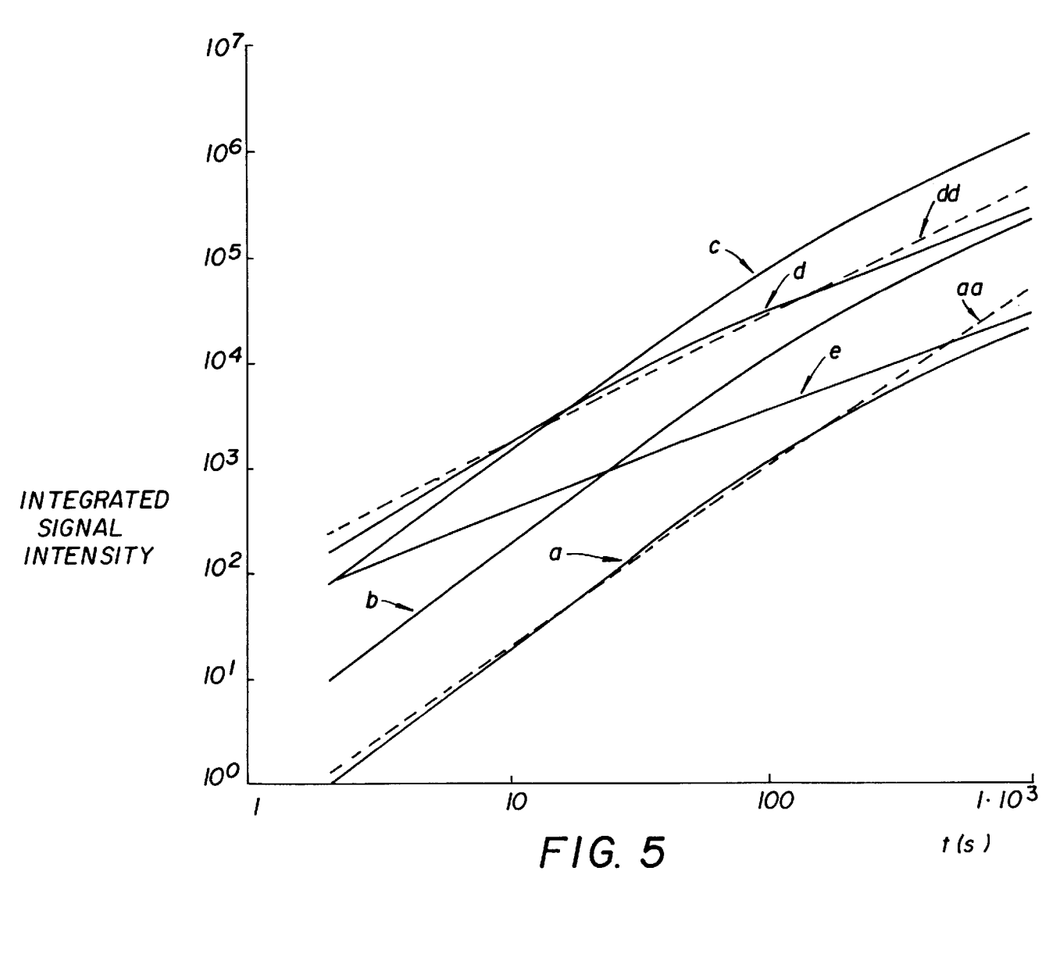
FIG. 5 shows plots of integrated signal intensity between time period 0–t as a function of time t at five different analyte concentrations.

FIGS. 4 and 5 describe the assay reaction kinetics i.e. the value of signal intensity as function of time. Since affinity constants used in this model are illustrative, the time axis must also be understood to be relative. Signal intensity is directly proportional to the concentration of product AbAgAb* formed in the reaction. FIG. 4 shows a transient signal intensity as a function of time t. FIG. 5 shows the integrated signal intensity between time period 0–t as a function of time t. the use of an integral improves the signal-to-noise ratio of the measurement. FIGS. 4 and 5 present signal intensity curves at different analyte concentrations: a) $10^{-11}$ mol/L, b) $10^{-10}$ mol/L, c) $10^{-9}$ mol/L, d) $10^{-8}$ mol/L and e) $10^{-7}$ mol/L. FIG. 6 shows a standard curve which represents concentration R of product AbAgAb* formed in the reaction as a function of concentration p of analyte Ag. The peak value of the response curve in the assay is marked as H in the FIG. 6.

FIG. 4 shows that the signal intensity growth rate is directly proportional to the concentration p of analyte Ag, i.e. a higher analyte concentration gives a higher signal intensity at specified time. As the reaction approaches equilibrium, the signal intensity curves incline asymptotically toward the equilibrium value (curves a, b and c). As soon as the analyte concentration p exceeds the binding capacity q of the solid phase, i.e. the concentration $10^{-9}$ mol/L in this example, the signal intensity rises, rapidly at first (curves d and e), but soon inclines to equilibrium which equals to the signal intensity at the lower analyte concentration. The curve cluster in FIG. 5 shows the total integrated signal intensity at a time span 0–t as a function of time at different analyte concentrations. In this case, the slope of curves a, b, c, d and e is less steep.

The curves presented in FIGS. 4 and 5 demonstrate the previously mentioned hook-effect so that when analyte concentrations exceed the binding capacity of the solid phase, the signal intensity remains at a certain level which is lower than the signal level for low concentrations. Moreover, the reaction equilibrium is reached much faster.

The growth of signal intensity and potential hook-effect may be anticipated by registering the growth rate dI/dt of signal intensity at different times t. When the reaction reaches equilibrium, the growth rate of the signal intensity drops to zero. When analyte concentrations exceed the binding capacity of the solid phase, the reaction equilibrium is reached earlier than with analyte concentrations lower than the binding capacity. By fitting a linear polynomial function or higher degree function, or any other function to the reaction curve at a specified time period, the concentration range of the analyte can be determined by using the adjusted fitting parameters. Monitoring of signal intensity growth rate is simple and noise-tolerant. Naturally, the adaptation of the curves may be done either on a linear or on a logarithmic scale. On the linear scale, the analyte concentration can be determined directly from the growth rate dI/dt of signal intensity.

As an example, the curves a and d in FIGS. 4 and 5 are fitted by using the first degree functions i.e. the lines on a logarithmic scale and at time span t=0–300 s. These lines are marked as 'aa' and 'dd', respectively. These regression lines are marked mathematically log[R(t)]=g log(t)+c, where R(t) is a time-dependent signal response, g is the slope of the regression line indicating reaction rate, and c is a constant indicating the value of the signal response at point t=1 s. Constant c also represents the concentration of the analyte.

By standardising a measuring device with known standard samples, the above mentioned kinetic signal responses for different concentrations of analyte Ag may be determined, and subsequently, the regression lines above determined. This results in a cluster of lines, the slope of which vary as a function of the analyte concentration Ag, when the analyte concentration exceeds the concentration corresponding to the peak value. A function can be fitted to the slope of this line cluster. An example of such a function fitted for the integral curves of FIG. 5, is presented in FIG. 6. This curve shows that in the assay response range, up until the peak value, the slope possess the same value, but as soon as the concentration of analyte Ag surpasses the peak value, the value of slope g drops sharply.

When an unknown sample is measured, the signal response and its integral is monitored until the reaction approaches equilibrium as presented earlier; and later, the value of the slope of the regression line is determined. By reading a corresponding sample concentration from the curve presented in FIG. 7, it can be ascertained if the concentration of the unknown sample is lower or higher than the concentration of the analyte at its peak value. If, the concentration is lower, the concentration of the unknown sample is read, after a specified reaction period, from the standard curve p=R'(R) presented in FIG. 6. On the other hand, if the concentration is within the range of the peak value, the concentration of the unknown sample is read from the curve p=G'(g) presented in FIG. 7. Finally, if the concentration surpasses the peak value, the concentration of the unknown sample may be read from either of the curves presented in FIGS. 6 and 7.

The fitted linear function used in the previous example for the growth rates of signal intensity is only illustrative. It is apparent that when the standard curve p=G'(g) is determined, other mathematical interpretation methods may also be used. For example, when higher degree polynomes are fitted for kinetic measuring curves, the coefficients of polynomes characterise the progress of the reaction. The coefficients may include information also from more complex reaction conditions. By examining these coefficients, the required response signals may be determined.

CONCLUSION

The microphotometric measurement system used for the device of this invention, can distinguish optically between the fluorescence emitted from the surface of the microparticles and the fluorescence emitted from the solution surrounding the particles. This resolution capability is based on the fact that in an appropriately diluted reaction suspension, only one microparticle at a time fits in the focal volume. The microparticles concentrate the reaction products and the concentration of the labels in terms of mol/L in the microscopic volume of the microparticle is many orders of magnitude higher that that of the free label molecules in the suspension. Consequently the background signal caused by free labelled reagents is minimal. Optical separation ensures sufficient resolution capability between free and bound fraction without chemical or physical separation.

Combining the features of this invention as described above with the microparticle based assay system allows a method and device for performing a fast, single-step biospecific assays for very small sample volumes of cell suspensions like whole blood or other clinical samples like serum samples. The assay is separation free and without risk of obtaining false analysis results for high concentrations because of the hook effect, since the hook-effect can be anticipated from the growth rate of the kinetic signal.

Characteristic of this invention is that the need of microfluidics liquid handling is minimised by focusing the laser beam directly into the reaction volume. This concept allows real time monitoring of the reaction kinetics. In addition the microparticle rate as well as the photon count rate can be made high using an active optical trapping and by the use of fluorescent nanoparticles for biospecific labelling. The real time monitoring further allows utilisation of the assay response beyond the hook point of the assay standard curve.

The method and the related device according to this invention can be realised in many different ways. However, an essential feature of this invention is that by directly focusing the laser beam into the reaction suspension, the progress of the reaction can be monitored, and that the biological material such as cells and in particular red cells cause insignificant background signal regardless of whether these cells are found in or out of the focal point. A statistically precise measurement result can be obtained in a short period of time because the detection duty cycle can be kept high by active trapping method. The fluorescence detector is activated only for the duration of the laser pulse used for two-photon excitation which means that photon emissions or thermal noise counts which occur between excitation intervals are not measured. Simultaneously, the photon detector can only be activated at the very moment the microparticle hits the focal volume.

Information about the position of microparticles at the focal volume is obtained, for example, through scattering and reflection at the laser beam wavelength. The best way to measure scattering is to use a confocal set-up. Scattering signal of the blood cells is smaller, because their relative refractive index is much lower than that of microparticles used in this method. Scattering and background caused by cells can be further reduced by perforating cell membranes with isotonic solution. As a result, intracellular fluids and haemoglobin are diluted in the assay suspension.

The method of this invention which is based on the use of two-photon excitation can also be a multiparametric assay as presented in international patent publication WO 96/22531. In this assay, microparticles are divided into many different categories and they are coated with various primary reagents binding different analytes. The manufacturing expenses of the measurement equipment in mind, it is extremely important that the excitation light used to detect particles, and the two-photon excitation of the label, can be performed with the same laser beam using either red or NIR range wavelength.

A specialist in the field appreciates that the different applications of the said invention may vary within the scope of the claims presented in the following section.

What is claimed is:

1. A method for detecting labeled complexes of bioreagents on microparticles in biospecific fluorometric assays, comprising:

contacting a bioaffinity binding solid phase comprising microparticles to which a primary biospecific reagent is bound simultaneously with a sample and a biospecific secondary reagent labeled with a fluorescent label in a reaction volume, thereby initiating a reaction, scanning a two-photon excitation focal volume within said reaction volume using a mechanical or optical scanner and a two-photon exciting laser beam which two-dimensionally optically traps the microparticles, momentarily interrupting or reducing the scanning speed of said two-photon excitation volume when said two-photon excitation volume approaches a microparticle randomly located in the reaction volume, optically trapping said microparticle such that it falls into a two-dimensional potential well created by said laser beam, and detecting fluorescence emission photon counts from said microparticle.

2. The method of claim 1, wherein said fluorescence emission photon counts from said microparticles are recorded only during time the microparticle remains in said two-photon excitation focal volume.

3. The method of claim 1, wherein said mechanical or optical scanner is optimized to measure as many particles per second as possible.

4. The method of claim 1, wherein momentary interruption or reduction of scanning is controlled by a signal obtained from a light scattering detector.

5. The method of claim 4, wherein said detector measures light scattering through a confocal optical set-up.

6. The method of claim 1, further comprising determining a growth rate parameter g from fluorescence emission photon counts from single microparticles at different times during the course of said reaction from unknown samples and from a series of standard samples diluted to different concentrations p from a reference material and correlating the growth rate parameter g obtained from the unknown samples with a standard curve $p=G'(g)$ derived from growth rate parameter g values obtained from the standard samples for determining the sample concentration p as function of the growth rate g, and/or determining a signal response R at an end point of said reaction from unknown samples and from a series of the standard samples diluted to different concentrations p and correlating the signal response R obtained from the unknown samples with a standard curve $p=R'(R)$ obtained from the standard samples for determining the sample concentration p as function of an end point response R.

7. The method of claim 6, wherein a concentration p of an analyte is determined on a basis of the standard curve $p=R'(R)$ or $p=G'(g)$ if the concentration p of the analyte is lower or higher than a concentration of the primary reagent, respectively.

8. The method of claim 7, wherein the growth rate parameter g is determined by fitting a polynomial function to a curve of the signal intensity measured as function of time and the concentration of the analyte p is determined from the coefficients of said polynomial function.

9. The method of claim 8, wherein the fitted function is of first order and the concentration of the analyte is determined from a slope of said function.

10. The method of claim 1, wherein the fluorescent label of the biospecific secondary reagent is a fluorescent nanoparticle.

11. The method of claim 1, wherein said laser beam is produced by a passively Q-switched Nd:YAG laser.

12. The method of claim 1, wherein said laser beam has a wavelength of 1064 nm.

13. The method of claim 12, wherein said laser beam is focused through an objective lens having a numerical aperture of from 0.65 to 0.8.

14. A device for detecting labeled complexes of bioreagents on microparticles in biospecific fluorometric assays, comprising:

a flat, hydrophobic, thin substrate onto which reaction components are dispensed to form a reaction volume in a form a droplet, such that the droplet maintains its form due to surface tension;

a laser which generates a laser beam of sufficient power to two-dimensionally optically trap and two-photon excite a fluorescent label attached to a primary biospecific reagent bound to a microparticle in said reaction volume;

an optical system for focusing said laser beam through an objective lens to a focal volume within said reaction volume, said objective lens having a numerical aperture optimized for two-dimensionally optically trapping an individual microparticle, wherein said system scans said focal volume at a predetermined speed within said reaction volume;

a detector which detects fluorescence emitted from said focal volume; and a control system for momentarily interrupting or reducing said predetermined scanning speed to a second, slower scanning speed when a microparticle is present in said focal volume, thereby allowing said microparticle to be optically trapped for a period of fluorescence detection by said laser beam during said period of fluorescence detection.

15. The device of claim 14 wherein said substrate is a tape made of plastic foil.

16. The device of claim 14, wherein said laser is a passively Q-switched Nd:YAG laser.

17. The device of claim 14, wherein said laser emits a laser beam having a wavelength of 1064 nm.

18. The device of claim 14 wherein said objective lens has a numerical aperture of from 0.65 to 0.8.

* * * * *